(12) United States Patent
Ostermaier et al.

(10) Patent No.: US 8,101,790 B2
(45) Date of Patent: Jan. 24, 2012

(54) PROCESS FOR IMPROVING ADIPONITRILE QUALITY

(75) Inventors: John J. Ostermaier, Orange, TX (US); Bruce E. Murphree, Beaumont, TX (US)

(73) Assignee: Invista North America S.A.R.L., Wilmington, DE (US)

( * ) Notice: Subject to any disclaimer, the term of this patent is extended or adjusted under 35 U.S.C. 154(b) by 731 days.

(21) Appl. No.: 12/137,925

(22) Filed: Jun. 12, 2008

(65) Prior Publication Data

US 2008/0319219 A1 Dec. 25, 2008

Related U.S. Application Data

(60) Provisional application No. 60/943,689, filed on Jun. 13, 2007.

(51) Int. Cl.
C07C 253/34 (2006.01)
(52) U.S. Cl. ...................................................... 558/456
(58) Field of Classification Search ................... 558/456
See application file for complete search history.

(56) References Cited

U.S. PATENT DOCUMENTS

| | | |
|---|---|---|
| 2,768,132 A | 10/1956 | Halliwell |
| 3,370,082 A | 2/1968 | Eisfeld et al. |
| 3,496,215 A | 2/1970 | Drinkard et al. |
| 3,496,217 A | 2/1970 | Drinkard, Jr. et al. |
| 3,496,218 A | 2/1970 | Drinkard, Jr. |
| 3,522,288 A | 7/1970 | Drinkard, Jr. et al. |
| 3,536,748 A | 10/1970 | Drinkard, Jr. et al. |
| 3,551,474 A | 12/1970 | Drinkard et al. |
| 3,564,040 A | 2/1971 | Downing et al. |
| 3,579,560 A | 5/1971 | Drinkard et al. |
| 3,655,723 A | 4/1972 | Drinkard, Jr. et al. |
| 3,694,485 A | 9/1972 | Drinkard, Jr. et al. |
| 3,725,459 A | 4/1973 | Yamada et al. |
| 3,752,839 A | 8/1973 | Drinkard, Jr. et al. |
| 3,758,545 A | 9/1973 | Pounder et al. |
| 3,766,231 A | 10/1973 | Gosser et al. |
| 3,766,237 A | 10/1973 | Chia et al. |
| 3,766,241 A | 10/1973 | Drinkard, Jr. et al. |
| 3,773,809 A | 11/1973 | Walter |
| 3,775,461 A | 11/1973 | Drinkard, Jr. et al. |
| 3,798,256 A | 3/1974 | King et al. |
| 3,803,206 A | 4/1974 | Nishimura et al. |
| 3,818,067 A | 6/1974 | Downing et al. |
| 3,818,068 A | 6/1974 | Wells |
| 3,846,474 A | 11/1974 | Mok |
| 3,849,472 A | 11/1974 | Waddan |
| 3,850,973 A | 11/1974 | Seidel et al. |
| 3,853,754 A | 12/1974 | Gosser |
| 3,853,948 A | 12/1974 | Drinkard, Jr. et al. |
| 3,864,380 A | 2/1975 | King et al. |
| 3,869,501 A | 3/1975 | Waddan |
| 3,920,721 A | 11/1975 | Gosser |
| 3,927,056 A | 12/1975 | Gosser |
| 3,947,487 A | 3/1976 | Crooks |
| 4,045,495 A | 8/1977 | Nazarenko et al. |
| 4,046,815 A | 9/1977 | Nazarenko |
| 4,076,756 A | 2/1978 | Nazarenko et al. |
| 4,087,452 A | 5/1978 | Kuntz |
| 4,146,555 A | 3/1979 | Kershaw |
| 4,147,717 A | 4/1979 | Kershaw |
| 4,177,215 A | 12/1979 | Seidel |
| 4,210,558 A | 7/1980 | Crooks |
| 4,230,634 A | 10/1980 | Benzie et al. |
| 4,240,976 A | 12/1980 | Benzie et al. |
| 4,251,468 A | 2/1981 | Nazarenko |
| 4,328,172 A | 5/1982 | Rapoport |
| 4,330,483 A | 5/1982 | Rapoport |
| 4,339,395 A | 7/1982 | Barnette et al. |
| 4,371,474 A | 2/1983 | Rapoport |
| 4,382,038 A | 5/1983 | McGill |
| 4,385,007 A | 5/1983 | Shook, Jr. |
| 4,416,824 A | 11/1983 | Reimer et al. |
| 4,416,825 A | 11/1983 | Ostermaier |
| 4,434,316 A | 2/1984 | Barnette |
| 4,539,302 A | 9/1985 | Leyendecker et al. |
| 4,705,881 A | 11/1987 | Rapoport |
| 4,749,801 A | 6/1988 | Bealty et al. |
| 4,774,353 A | 9/1988 | Hall et al. |
| 4,874,884 A | 10/1989 | McKinney et al. |
| 4,952,541 A | 8/1990 | Heckle et al. |
| 4,990,645 A | 2/1991 | Back et al. |
| 5,107,012 A | 4/1992 | Grunewald |
| 5,302,756 A | 4/1994 | McKinney |
| 5,312,959 A | 5/1994 | Sieja et al. |
| 5,449,807 A | 9/1995 | Druliner |
| 5,488,129 A | 1/1996 | Huser et al. |

(Continued)

FOREIGN PATENT DOCUMENTS

AU 6522096 2/1997

(Continued)

OTHER PUBLICATIONS

Harnby et al., Mixing in the Process Industries, 2nd edition, Butterworth Heinemann (1992) [ book furnished upon request ].

(Continued)

Primary Examiner — Joseph Kosack

(57) ABSTRACT

A process and apparatus for reacting deleterious impurities contained in adiponitrile (ADN) comprises feeding ADN and an ozone containing gas into a co-current plug flow reactor containing static mixer elements, to oxidize at least a portion of the impurities, thereby producing a reactor discharge, which is processed to produce an ozone-treated ADN product.

23 Claims, 2 Drawing Sheets

U.S. PATENT DOCUMENTS

| | | | |
|---|---|---|---|
| 5,512,695 | A | 4/1996 | Kreutzer et al. |
| 5,512,696 | A | 4/1996 | Kreutzer et al. |
| 5,523,453 | A | 6/1996 | Breikss |
| 5,543,536 | A | 8/1996 | Tam |
| 5,663,369 | A | 9/1997 | Kreutzer et al. |
| 5,688,986 | A | 11/1997 | Tam et al. |
| 5,696,280 | A | 12/1997 | Shapiro |
| 5,709,841 | A | 1/1998 | Reimer |
| 5,723,641 | A | 3/1998 | Tam et al. |
| 5,773,637 | A | 6/1998 | Cicha et al. |
| 5,821,378 | A | 10/1998 | Foo et al. |
| 5,847,191 | A | 12/1998 | Bunel et al. |
| 5,856,555 | A | 1/1999 | Huser et al. |
| 5,908,805 | A | 6/1999 | Huser et al. |
| 5,959,135 | A | 9/1999 | Garner et al. |
| 6,090,987 | A | 7/2000 | Billig et al. |
| 6,121,184 | A | 9/2000 | Druliner et al. |
| 6,147,247 | A | 11/2000 | Voit et al. |
| 6,169,198 | B1 | 1/2001 | Fischer et al. |
| 6,171,996 | B1 | 1/2001 | Garner et al. |
| 6,197,992 | B1 | 3/2001 | Fischer et al. |
| 6,242,633 | B1 | 6/2001 | Fischer et al. |
| 6,284,865 | B1 | 9/2001 | Tam et al. |
| 6,307,109 | B1 | 10/2001 | Kanel et al. |
| 6,331,651 | B1 * | 12/2001 | Ostermaier .................. 564/490 |
| 6,355,833 | B2 | 3/2002 | Fischer et al. |
| 6,359,178 | B1 | 3/2002 | Fischer et al. |
| 6,461,481 | B1 | 10/2002 | Barnette et al. |
| 6,469,194 | B2 | 10/2002 | Burattin et al. |
| 6,521,778 | B1 | 2/2003 | Fischer et al. |
| 6,646,148 | B1 | 11/2003 | Kreutzer |
| 6,660,877 | B2 | 12/2003 | Lenges et al. |
| 6,737,539 | B2 | 5/2004 | Lenges et al. |
| 6,753,440 | B2 | 6/2004 | Druliner et al. |
| 6,770,770 | B1 | 8/2004 | Baumann et al. |
| 6,846,945 | B2 | 1/2005 | Lenges et al. |
| 6,852,199 | B2 | 2/2005 | Jungkamp et al. |
| 6,855,799 | B2 | 2/2005 | Tam et al. |
| 6,897,329 | B2 | 5/2005 | Jackson et al. |
| 6,984,604 | B2 | 1/2006 | Cobb et al. |
| 7,022,866 | B2 | 4/2006 | Bartsch et al. |
| 7,067,685 | B2 | 6/2006 | Bartsch et al. |
| 7,084,293 | B2 | 8/2006 | Rosier et al. |
| 7,084,294 | B2 | 8/2006 | Jungkamp et al. |
| 7,098,358 | B2 | 8/2006 | Burattin et al. |
| 7,105,696 | B2 | 9/2006 | Burattin et al. |
| 7,253,298 | B2 | 8/2007 | Galland et al. |
| 7,345,006 | B2 | 3/2008 | Bartsch et al. |
| 7,381,845 | B2 | 6/2008 | Weiskopf et al. |
| 7,439,381 | B2 | 10/2008 | Jungkamp et al. |
| 7,442,825 | B2 | 10/2008 | Galland et al. |
| 7,470,805 | B2 | 12/2008 | Rosier et al. |
| 7,521,575 | B2 | 4/2009 | Bartsch et al. |
| 7,528,275 | B2 | 5/2009 | Bartsch et al. |
| 7,538,240 | B2 | 5/2009 | Jungkamp et al. |
| 7,541,486 | B2 | 6/2009 | Scheidel et al. |
| 7,700,795 | B2 | 4/2010 | Haderlein et al. |
| 2003/0135014 | A1 | 7/2003 | Radu et al. |
| 2003/0212298 | A1 | 11/2003 | Brasse et al. |
| 2004/0063991 | A1 | 4/2004 | Burattin et al. |
| 2004/0176622 | A1 | 9/2004 | Bartsch et al. |
| 2004/0235648 | A1 | 11/2004 | Bartsch et al. |
| 2004/0260112 | A1 | 12/2004 | Basset et al. |
| 2005/0090677 | A1 | 4/2005 | Bartsch et al. |
| 2005/0090678 | A1 | 4/2005 | Bartsch et al. |
| 2005/0247624 | A1 | 11/2005 | Jungkamp et al. |
| 2006/0142609 | A1 | 6/2006 | Bourgeois et al. |
| 2006/0175189 | A1 | 8/2006 | Gerber et al. |
| 2006/0252955 | A1 | 11/2006 | Rosier et al. |
| 2006/0258873 | A1 | 11/2006 | Rosier et al. |
| 2006/0258874 | A1 | 11/2006 | Bartsch et al. |
| 2006/0264651 | A1 | 11/2006 | Bartsch et al. |
| 2007/0060766 | A1 | 3/2007 | Bartsch et al. |
| 2007/0073071 | A1 | 3/2007 | Haderlein et al. |
| 2007/0083057 | A1 | 4/2007 | Haderlein et al. |
| 2007/0088173 | A1 | 4/2007 | Haderlein et al. |
| 2007/0112215 | A1 | 5/2007 | Jungkamp et al. |
| 2007/0155977 | A1 | 7/2007 | Jungkamp et al. |
| 2007/0155978 | A1 | 7/2007 | Jungkamp et al. |
| 2007/0155980 | A1 | 7/2007 | Scheidel et al. |
| 2008/0015378 | A1 | 1/2008 | Foo et al. |
| 2008/0015380 | A1 | 1/2008 | Foo et al. |
| 2008/0015381 | A1 | 1/2008 | Foo et al. |
| 2008/0015382 | A1 | 1/2008 | Foo et al. |
| 2008/0071105 | A1 | 3/2008 | Bartsch et al. |
| 2008/0076944 | A1 | 3/2008 | Bartsch et al. |
| 2008/0083607 | A1 | 4/2008 | Deckert et al. |
| 2008/0221351 | A1 | 9/2008 | Bartsch et al. |
| 2008/0227214 | A1 | 9/2008 | Jungkamp et al. |
| 2008/0227998 | A1 | 9/2008 | Scheidel et al. |
| 2008/0242883 | A1 | 10/2008 | Jungkamp et al. |
| 2008/0242885 | A1 | 10/2008 | Jungkamp et al. |
| 2008/0242886 | A1 | 10/2008 | Bartsch et al. |
| 2008/0275266 | A1 | 11/2008 | Bartsch et al. |
| 2008/0281119 | A1 | 11/2008 | Scheidel et al. |
| 2008/0281120 | A1 | 11/2008 | Jungkamp et al. |
| 2009/0054671 | A1 | 2/2009 | Haderlein et al. |

FOREIGN PATENT DOCUMENTS

| | | |
|---|---|---|
| AU | 199665220 A | 2/1997 |
| CA | 672712 | 10/1963 |
| CA | 1324613 C | 11/1993 |
| CA | 2462720 A1 | 4/2003 |
| CA | 2552862 A1 | 8/2005 |
| CN | 1113854 A | 12/1995 |
| CN | 1145531 A | 3/1997 |
| CN | 1146166 A | 3/1997 |
| CN | 1146762 A | 4/1997 |
| CN | 1159106 A | 9/1997 |
| CN | 1159799 A | 9/1997 |
| CN | 1163606 A | 10/1997 |
| CN | 1169143 A | 12/1997 |
| CN | 1173935 A | 2/1998 |
| CN | 1179147 A | 4/1998 |
| CN | 1198151 A | 11/1998 |
| CN | 1204111 A | 1/1999 |
| CN | 1206357 A | 1/1999 |
| CN | 1211931 A | 3/1999 |
| CN | 1045591 C | 10/1999 |
| CN | 1236355 A | 11/1999 |
| CN | 1047163 C | 12/1999 |
| CN | 1245489 A | 2/2000 |
| CN | 1247102 A | 3/2000 |
| CN | 1052718 C | 5/2000 |
| CN | 1265094 A | 8/2000 |
| CN | 1266424 A | 9/2000 |
| CN | 1270543 A | 10/2000 |
| CN | 1068307 C | 7/2001 |
| CN | 1304334 A | 7/2001 |
| CN | 1069310 C | 8/2001 |
| CN | 1072980 C | 10/2001 |
| CN | 1076342 C | 12/2001 |
| CN | 1327881 A | 12/2001 |
| CN | 1331843 A | 1/2002 |
| CN | 1333745 A | 1/2002 |
| CN | 1082946 C | 4/2002 |
| CN | 1344180 A | 4/2002 |
| CN | 1356335 A | 7/2002 |
| CN | 1387534 A | 12/2002 |
| CN | 1099912 C | 1/2003 |
| CN | 1390241 A | 1/2003 |
| CN | 1103613 C | 3/2003 |
| CN | 1106218 C | 4/2003 |
| CN | 1108643 C | 5/2003 |
| CN | 1427807 A | 7/2003 |
| CN | 1449400 A | 10/2003 |
| CN | 1461295 A | 12/2003 |
| CN | 1471510 A | 1/2004 |
| CN | 1141285 C | 3/2004 |
| CN | 1142224 C | 3/2004 |
| CN | 1144781 C | 4/2004 |
| CN | 1487917 A | 4/2004 |
| CN | 1152855 C | 6/2004 |
| CN | 1535179 A | 10/2004 |
| CN | 1564807 A | 1/2005 |
| CN | 1568225 A | 1/2005 |
| CN | 1568226 A | 1/2005 |

| | | | | | | | |
|---|---|---|---|---|---|---|---|
| CN | 1617892 | A | 5/2005 | EP | 792259 | B1 | 8/1999 |
| CN | 1617900 | A | 5/2005 | EP | 804412 | B1 | 12/1999 |
| CN | 1212293 | C | 7/2005 | EP | 1000019 | A1 | 5/2000 |
| CN | 1639176 | A | 7/2005 | EP | 1001928 | A1 | 5/2000 |
| CN | 1213051 | C | 8/2005 | EP | 1003716 | A1 | 5/2000 |
| CN | 1665776 | A | 9/2005 | EP | 1019190 | A1 | 7/2000 |
| CN | 1670139 | A | 9/2005 | EP | 755302 | B1 | 10/2000 |
| CN | 1674989 | A | 9/2005 | EP | 929513 | B1 | 4/2001 |
| CN | 1675172 | A | 9/2005 | EP | 881924 | B1 | 5/2001 |
| CN | 1222358 | C | 10/2005 | EP | 854858 | B1 | 6/2001 |
| CN | 1732148 | A | 2/2006 | EP | 815073 | B1 | 7/2001 |
| CN | 1735460 | A | 2/2006 | EP | 1144114 | A3 | 9/2001 |
| CN | 1245489 | C | 3/2006 | EP | 1091804 | B1 | 2/2002 |
| CN | 1740183 | A | 3/2006 | EP | 944585 | B1 | 4/2002 |
| CN | 1745062 | A | 3/2006 | EP | 1000019 | B1 | 2/2003 |
| CN | 1767895 | A | 5/2006 | EP | 911339 | B1 | 4/2003 |
| CN | 1260009 | C | 6/2006 | EP | 1216268 | B1 | 11/2003 |
| CN | 1266424 | C | 7/2006 | EP | 1350788 | A3 | 11/2003 |
| CN | 1270543 | C | 8/2006 | EP | 1003607 | B1 | 12/2003 |
| CN | 1274671 | C | 9/2006 | EP | 1003716 | B1 | 2/2004 |
| CN | 1274699 | C | 9/2006 | EP | 1313743 | B1 | 3/2004 |
| CN | 1835915 | A | 9/2006 | EP | 1414567 | A1 | 5/2004 |
| CN | 1279088 | C | 10/2006 | EP | 1427695 | A1 | 6/2004 |
| CN | 1847288 | A | 10/2006 | EP | 1438133 | A1 | 7/2004 |
| CN | 1283620 | C | 11/2006 | EP | 1019190 | B1 | 12/2004 |
| CN | 1857775 | A | 11/2006 | EP | 1140801 | B1 | 2/2005 |
| CN | 1289539 | C | 12/2006 | EP | 1395547 | B1 | 3/2005 |
| CN | 1293942 | C | 1/2007 | EP | 1001928 | B1 | 4/2005 |
| CN | 1906150 | A | 1/2007 | EP | 1521736 | A1 | 4/2005 |
| CN | 1914154 | A | 2/2007 | EP | 1521737 | A1 | 4/2005 |
| CN | 1914155 | A | 2/2007 | EP | 1521738 | A2 | 4/2005 |
| CN | 1914156 | A | 2/2007 | EP | 1603865 | A1 | 12/2005 |
| CN | 1914157 | A | 2/2007 | EP | 1324976 | B1 | 2/2006 |
| CN | 1914158 | A | 2/2007 | EP | 1214975 | B1 | 3/2006 |
| CN | 1914159 | A | 2/2007 | EP | 1324978 | B1 | 3/2006 |
| CN | 1914160 | A | 2/2007 | EP | 1648860 | A1 | 4/2006 |
| CN | 1914161 | A | 2/2007 | EP | 891323 | B1 | 6/2006 |
| CN | 1914162 | A | 2/2007 | EP | 1226147 | B1 | 6/2006 |
| CN | 1914165 | A | 2/2007 | EP | 1438317 | B1 | 6/2006 |
| CN | 1914166 | A | 2/2007 | EP | 1682561 | A1 | 7/2006 |
| CN | 1914167 | A | 2/2007 | EP | 1448668 | B1 | 8/2006 |
| CN | 1914216 | A | 2/2007 | EP | 1587621 | B1 | 8/2006 |
| CN | 1307237 | C | 3/2007 | EP | 1713759 | A1 | 10/2006 |
| CN | 1315790 | C | 5/2007 | EP | 1713761 | A1 | 10/2006 |
| CN | 1318432 | C | 5/2007 | EP | 1713762 | A1 | 10/2006 |
| CN | 1997624 | A | 7/2007 | EP | 1713766 | A1 | 10/2006 |
| CN | 1331843 | C | 8/2007 | EP | 1716102 | A2 | 11/2006 |
| CN | 101020641 | A | 8/2007 | EP | 1716103 | A1 | 11/2006 |
| CN | 101035799 | A | 9/2007 | EP | 1716104 | A1 | 11/2006 |
| CN | 101043946 | A | 9/2007 | EP | 1716105 | A1 | 11/2006 |
| CN | 100348322 | C | 11/2007 | EP | 1716106 | A1 | 11/2006 |
| CN | 100351227 | C | 11/2007 | EP | 1716107 | A1 | 11/2006 |
| CN | 100352824 | C | 12/2007 | EP | 1716109 | A2 | 11/2006 |
| CN | 100361966 | C | 1/2008 | EP | 1610893 | B1 | 3/2007 |
| CN | 100364666 | C | 1/2008 | EP | 1621531 | B1 | 3/2007 |
| DE | 1807088 | U | 3/1960 | EP | 1438132 | B1 | 4/2007 |
| DE | 1807088 | A1 | 6/1969 | EP | 1799697 | A1 | 6/2007 |
| DE | 2055747 | A1 | 5/1971 | EP | 1713764 | B1 | 8/2007 |
| DE | 1593277 | B2 | 8/1973 | EP | 1713816 | B1 | 8/2007 |
| DE | 1593277 | C3 | 3/1974 | EP | 1825914 | A1 | 8/2007 |
| DE | 2700904 | C2 | 10/1983 | EP | 1448620 | B1 | 6/2008 |
| DE | 68909466 | T2 | 3/1994 | EP | 1817108 | B1 | 6/2008 |
| DE | 10136488 | A1 | 2/2003 | EP | 1713760 | B1 | 7/2008 |
| DE | 10150285 | A1 | 4/2003 | EP | 1571172 | B1 | 10/2008 |
| DE | 10350999 | A1 | 6/2005 | EP | 1988998 | A1 | 11/2008 |
| DE | 102004004696 | A1 | 8/2005 | EP | 1265832 | B1 | 5/2009 |
| EP | 0001899 | B1 | 3/1982 | EP | 1592659 | B1 | 7/2009 |
| EP | 123438 | B1 | 7/1987 | EP | 1586598 | B1 | 9/2009 |
| EP | 160296 | B1 | 10/1988 | EP | 2098106 | A1 | 9/2009 |
| EP | 268448 | B1 | 9/1991 | EP | 1567478 | B1 | 10/2009 |
| EP | 510689 | A1 | 10/1992 | EP | 1682559 | B1 | 12/2009 |
| EP | 248643 | B1 | 3/1993 | EP | 1630166 | B1 | 2/2010 |
| EP | 336314 | B1 | 9/1993 | FR | 1544656 | A | 11/1968 |
| EP | 464691 | B1 | 12/1993 | FR | 2015115 | A5 | 4/1970 |
| EP | 675871 | B1 | 4/1997 | FR | 1603513 | A | 5/1971 |
| EP | 634395 | B1 | 9/1997 | FR | 2069411 | A5 | 9/1971 |
| EP | 650959 | B1 | 9/1997 | FR | 2845379 | B1 | 12/2004 |
| EP | 784610 | B1 | 2/1999 | FR | 2873696 | A1 | 2/2006 |
| EP | 757672 | B1 | 6/1999 | FR | 2873696 | B1 | 10/2006 |

| | | | | | | | |
|---|---|---|---|---|---|---|---|
| GB | 0219474 | A | 7/1924 | JP | 11507297 | A | 6/1999 |
| GB | 1104140 | A | 2/1968 | JP | 03001298 | B2 | 1/2000 |
| GB | 1203702 | A | 9/1970 | JP | 03069915 | B2 | 7/2000 |
| GB | 1213175 | A | 11/1970 | JP | 2001500135 | A | 1/2001 |
| GB | 1429169 | A | 3/1976 | JP | 2001506250 | A | 5/2001 |
| GB | 1429621 | A | 3/1976 | JP | 2001512097 | A | 8/2001 |
| GB | 1436932 | A | 5/1976 | JP | 03205587 | B2 | 9/2001 |
| GB | 1458322 | A | 12/1976 | JP | 2001516640 | A | 10/2001 |
| GB | 1482909 | A | 8/1977 | JP | 03285878 | B2 | 5/2002 |
| GB | 2007521 | A | 5/1979 | JP | 2002517473 | A | 6/2002 |
| GB | 1565443 | A | 4/1980 | JP | 03320424 | B2 | 9/2002 |
| GB | 1594694 | A | 8/1981 | JP | 2002533321 | A | 10/2002 |
| GB | 2007521 | B | 6/1982 | JP | 03380543 | B2 | 2/2003 |
| HK | 1025950 | A1 | 7/2003 | JP | 2003510385 | A | 3/2003 |
| HK | 1026383 | A1 | 7/2004 | JP | 2003526688 | A | 9/2003 |
| HK | 1052364 | A1 | 5/2007 | JP | 03478399 | B2 | 12/2003 |
| JP | 48028423 | Y1 | 8/1973 | JP | 2004501058 | A | 1/2004 |
| JP | 48028423 | B | 9/1973 | JP | 2004507550 | A | 3/2004 |
| JP | 49043924 | Y1 | 12/1974 | JP | 03519410 | B2 | 4/2004 |
| JP | 50059324 | U | 6/1975 | JP | 03535172 | B2 | 6/2004 |
| JP | 50059326 | U | 6/1975 | JP | 03553952 | B2 | 8/2004 |
| JP | 51007649 | B | 3/1976 | JP | 2004534032 | A | 11/2004 |
| JP | 52012698 | B | 4/1977 | JP | 2004535929 | A | 12/2004 |
| JP | 1013127 | C | 9/1980 | JP | 03621133 | B2 | 2/2005 |
| JP | 55047031 | B | 11/1980 | JP | 2005503410 | A | 2/2005 |
| JP | 57156454 | U | 10/1982 | JP | 2005505610 | A | 2/2005 |
| JP | 57156455 | U | 10/1982 | JP | 2005505611 | A | 2/2005 |
| JP | 57179144 | U | 11/1982 | JP | 2005510588 | A | 4/2005 |
| JP | 1136333 | C | 2/1983 | JP | 2005510605 | A | 4/2005 |
| JP | 58067658 | U | 5/1983 | JP | 2004509942 | | 10/2005 |
| JP | 58126892 | U | 8/1983 | JP | 2005533095 | A | 11/2005 |
| JP | 1170710 | C | 10/1983 | JP | 2005533096 | A | 11/2005 |
| JP | 58159452 | U | 10/1983 | JP | 2005538075 | A | 12/2005 |
| JP | 60044295 | A | 3/1985 | JP | 03739404 | B2 | 1/2006 |
| JP | 60044295 | B | 10/1985 | JP | 2004534032 | | 1/2006 |
| JP | 62294691 | A | 12/1987 | JP | 2004535929 | | 1/2006 |
| JP | 63135363 | U | 9/1988 | JP | 2006000451 | A | 1/2006 |
| JP | 1013127 | Y2 | 4/1989 | JP | 2006511591 | A | 4/2006 |
| JP | 1209830 | A | 8/1989 | JP | 2006519797 | A | 8/2006 |
| JP | 1136333 | U | 9/1989 | JP | 2006528616 | A | 12/2006 |
| JP | 1050220 | B | 10/1989 | JP | 2007083057 | A | 4/2007 |
| JP | 1173751 | U | 12/1989 | JP | 2007509885 | A | 4/2007 |
| JP | 1565159 | C | 6/1990 | JP | 2007509886 | A | 4/2007 |
| JP | 3001298 | B | 1/1991 | JP | 2007509887 | A | 4/2007 |
| JP | 1615749 | C | 8/1991 | JP | 2007519516 | A | 7/2007 |
| JP | 3205587 | A | 9/1991 | JP | 2007519663 | A | 7/2007 |
| JP | 1627124 | C | 11/1991 | JP | 2007519664 | A | 7/2007 |
| JP | 1627146 | C | 11/1991 | JP | 2007519666 | A | 7/2007 |
| JP | 3069915 | B | 11/1991 | JP | 2007519667 | A | 7/2007 |
| JP | 3285878 | A | 12/1991 | JP | 2007519670 | A | 7/2007 |
| JP | 1642102 | C | 2/1992 | JP | 2007519671 | A | 7/2007 |
| JP | 4012248 | Y2 | 3/1992 | JP | 2007519672 | A | 7/2007 |
| JP | 4057050 | U | 5/1992 | JP | 2007519673 | A | 7/2007 |
| JP | 4166155 | A | 6/1992 | JP | 2007519674 | A | 7/2007 |
| JP | 4230254 | A | 8/1992 | JP | 2007519675 | A | 7/2007 |
| JP | 4057050 | B | 9/1992 | JP | 2007519677 | A | 7/2007 |
| JP | 4060532 | B | 9/1992 | JP | 2007522122 | A | 8/2007 |
| JP | 4118676 | U | 10/1992 | JP | 04012248 | B2 | 11/2007 |
| JP | 4128141 | U | 11/1992 | JP | 2006515323 | | 2/2008 |
| JP | 1729140 | C | 1/1993 | JP | 04057050 | B2 | 3/2008 |
| JP | 1811422 | C | 12/1993 | JP | 04060532 | B2 | 3/2008 |
| JP | 7025841 | Y2 | 6/1995 | JP | 2006512918 | | 3/2008 |
| JP | 7188144 | A | 7/1995 | JP | 2008515831 | A | 5/2008 |
| JP | 2037346 | C | 3/1996 | JP | 2008516907 | A | 5/2008 |
| JP | 8504814 | A | 5/1996 | JP | 04118676 | B2 | 7/2008 |
| JP | 8157795 | A | 6/1996 | JP | 04128141 | B2 | 7/2008 |
| JP | 2098106 | C | 10/1996 | JP | 04166155 | B2 | 10/2008 |
| JP | 2521777 | Y2 | 1/1997 | JP | 04230254 | B2 | 2/2009 |
| JP | 02623448 | B2 | 6/1997 | KR | 198802621 | Y1 | 7/1988 |
| JP | 9505586 | A | 6/1997 | KR | 198802296 | B | 10/1988 |
| JP | 9512013 | A | 12/1997 | KR | 198802296 | B1 | 10/1988 |
| JP | 10505101 | A | 5/1998 | KR | 199003458 | B1 | 5/1990 |
| JP | 10506911 | A | 7/1998 | KR | 199008166 | B1 | 11/1990 |
| JP | 10509954 | A | 9/1998 | KR | 199104132 | B1 | 6/1991 |
| JP | 02818503 | B2 | 10/1998 | KR | 199205087 | Y1 | 7/1992 |
| JP | 10512879 | A | 12/1998 | KR | 2006132885 | A | 12/2006 |
| JP | 11501660 | A | 2/1999 | MX | 2004PA002764 | A | 6/2004 |
| JP | 11504262 | A | 4/1999 | NL | 197700262 | A | 7/1977 |
| JP | 02911608 | B2 | 6/1999 | NL | 188158 | C | 4/1992 |

| | | | | | | |
|---|---|---|---|---|---|---|
| SU | 276033 | 5/1972 | | WO | WO03024919 A1 | 3/2003 |
| SU | 677650 A | 7/1979 | | WO | WO03031392 A1 | 4/2003 |
| TW | 387874 B | 4/2000 | | WO | WO03033141 A1 | 4/2003 |
| TW | 400249 B | 8/2000 | | WO | WO03033509 A1 | 4/2003 |
| TW | 453983 B | 9/2001 | | WO | WO03046019 A1 | 6/2003 |
| TW | 453985 B | 9/2001 | | WO | WO03046049 A1 | 6/2003 |
| TW | 455576 B | 9/2001 | | WO | WO03068729 A1 | 8/2003 |
| TW | 457244 B | 10/2001 | | WO | WO03076394 A1 | 9/2003 |
| TW | 458959 B | 10/2001 | | WO | WO2004007431 A1 | 1/2004 |
| TW | 519496 B | 2/2003 | | WO | WO2004007432 A1 | 1/2004 |
| TW | 527340 B | 4/2003 | | WO | WO2004007435 A2 | 1/2004 |
| TW | 576837 B | 2/2004 | | WO | WO2004007508 A2 | 1/2004 |
| TW | 580489 B | 3/2004 | | WO | WO2004060855 A1 | 7/2004 |
| TW | 580490 B | 3/2004 | | WO | WO2004064994 A2 | 8/2004 |
| TW | 584623 B | 4/2004 | | WO | WO2004065352 A2 | 8/2004 |
| TW | 592821 B | 6/2004 | | WO | WO2004080924 A2 | 9/2004 |
| TW | 226345 B | 1/2005 | | WO | WO2004080948 A1 | 9/2004 |
| TW | 233438 B | 6/2005 | | WO | WO2004087314 A1 | 10/2004 |
| TW | 245780 B | 12/2005 | | WO | WO2005019160 A1 | 3/2005 |
| TW | 266650 B | 11/2006 | | WO | WO2005042156 A1 | 5/2005 |
| WO | WO7900193 A1 | 4/1979 | | WO | WO2005042157 A2 | 5/2005 |
| WO | WO9414752 A1 | 7/1994 | | WO | WO2005042547 A1 | 5/2005 |
| WO | WO9514659 A1 | 6/1995 | | WO | WO2005042549 A1 | 5/2005 |
| WO | WO9528228 A1 | 10/1995 | | WO | WO2005073167 A1 | 8/2005 |
| WO | WO9529153 A1 | 11/1995 | | WO | WO2005073168 A1 | 8/2005 |
| WO | WO9611182 A1 | 4/1996 | | WO | WO2005073169 A1 | 8/2005 |
| WO | WO9616022 A1 | 5/1996 | | WO | WO2005073170 A1 | 8/2005 |
| WO | WO9622968 A1 | 8/1996 | | WO | WO2005073171 A1 | 8/2005 |
| WO | WO9629303 A1 | 9/1996 | | WO | WO2005073172 A1 | 8/2005 |
| WO | WO9703040 A1 | 1/1997 | | WO | WO2005073173 A1 | 8/2005 |
| WO | WO9712857 A1 | 4/1997 | | WO | WO2005073174 A1 | 8/2005 |
| WO | WO9724183 A1 | 7/1997 | | WO | WO2005073175 A1 | 8/2005 |
| WO | WO9736855 A2 | 10/1997 | | WO | WO2005073176 A1 | 8/2005 |
| WO | WO9811051 A1 | 3/1998 | | WO | WO2005073178 A2 | 8/2005 |
| WO | WO9827054 A1 | 6/1998 | | WO | WO2005073179 A1 | 8/2005 |
| WO | WO9906146 A2 | 2/1999 | | WO | WO2005073241 A1 | 8/2005 |
| WO | WO9906356 | 2/1999 | | WO | WO2006040023 A1 | 4/2006 |
| WO | WO9906359 A1 | 2/1999 | | WO | WO2006042675 A2 | 4/2006 |
| WO | WO9913983 A1 | 3/1999 | | WO | WO2005073166 A3 | 3/2007 |
| WO | WO9964155 A1 | 12/1999 | | WO | WO2007051374 A1 | 5/2007 |
| WO | WO00/03972 | 1/2000 | | WO | WO2007096274 A1 | 8/2007 |
| WO | WO0001485 A2 | 1/2000 | | WO | 2007115936 | 10/2007 |
| WO | WO0037431 A1 | 6/2000 | | WO | WO2007115936 A2 | 10/2007 |
| WO | WO0121684 A1 | 3/2001 | | WO | WO2008008926 A2 | 1/2008 |
| WO | WO0136429 A1 | 5/2001 | | WO | WO2008008928 A2 | 1/2008 |
| WO | WO0168247 A2 | 9/2001 | | WO | WO2008008929 A2 | 1/2008 |
| WO | WO0168247 A8 | 9/2001 | | WO | WO2008008930 A2 | 1/2008 |
| WO | WO0211108 A1 | 2/2002 | | WO | WO2008028843 A1 | 3/2008 |
| WO | WO0213964 A2 | 2/2002 | | WO | WO2008062058 A1 | 5/2008 |
| WO | WO0218392 A1 | 3/2002 | | | | |
| WO | WO0226698 A1 | 4/2002 | | | | |
| WO | WO0230854 A2 | 4/2002 | | | | |
| WO | WO02053527 A1 | 7/2002 | | | | |
| WO | WO02092551 A2 | 11/2002 | | | | |
| WO | WO03011457 A1 | 2/2003 | | | | |
| WO | WO03018540 A1 | 3/2003 | | | | |

OTHER PUBLICATIONS

Chemical Reaction Engineering, 3rd edition by Octave Levenspiel, Wiley—Chapters 23 and 24, 1999.

* cited by examiner

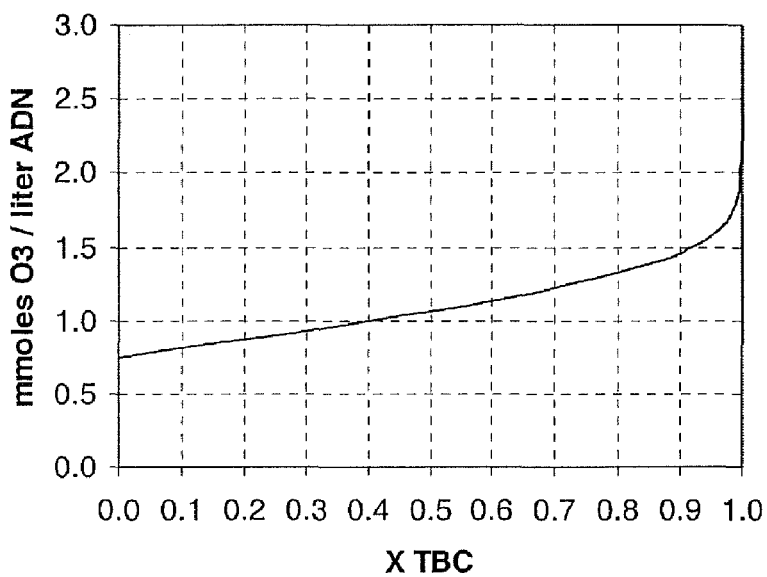
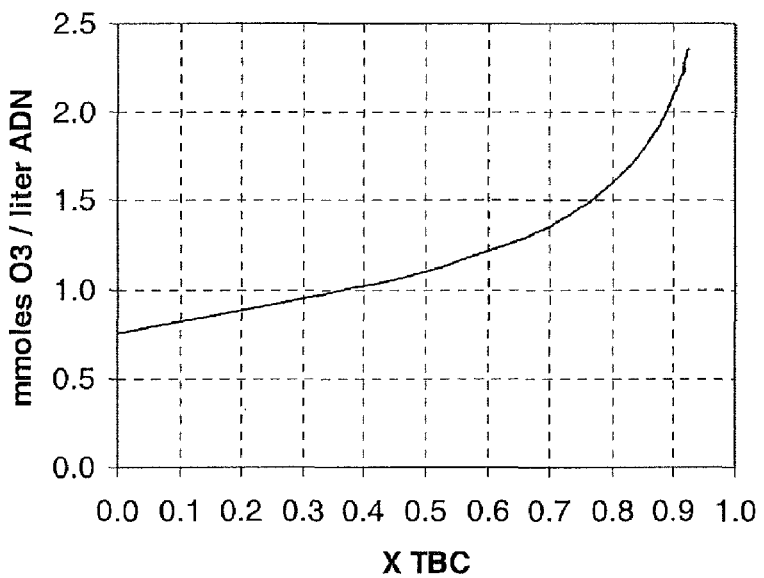

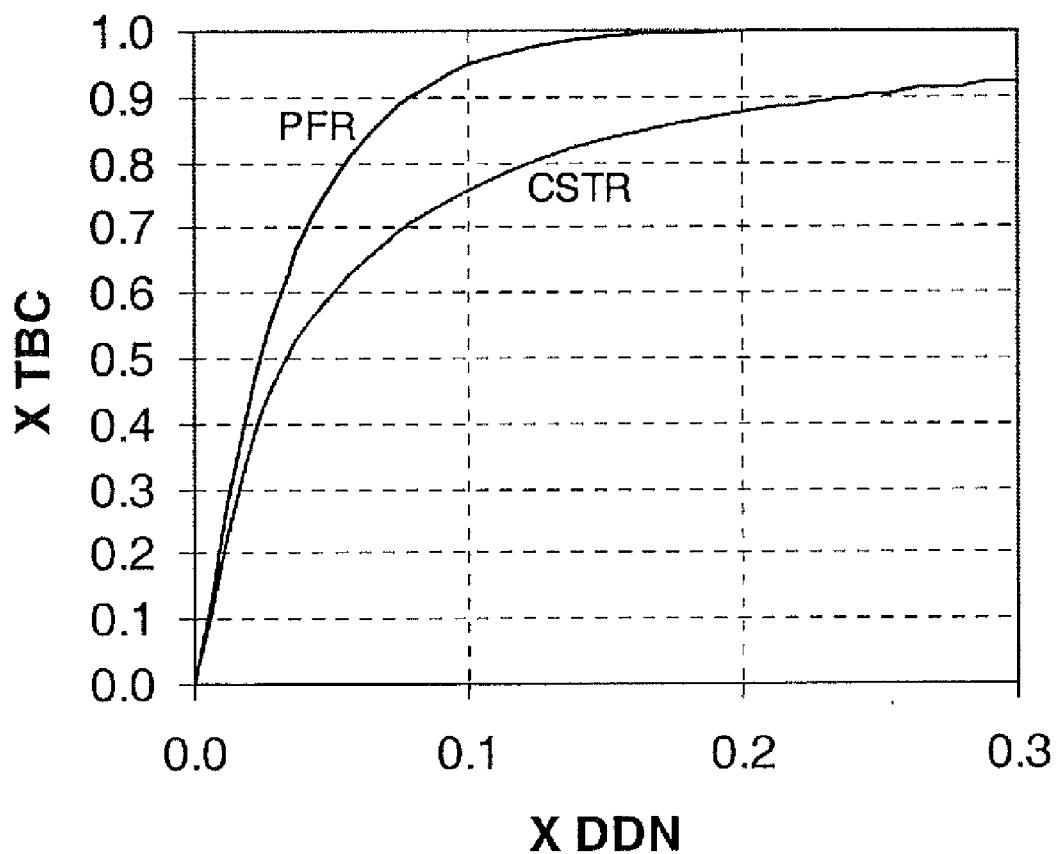

PROCESS FOR IMPROVING ADIPONITRILE QUALITY

FIELD OF THE INVENTION

This invention relates to a process and apparatus for improving the quality of adiponitrile (ADN). The invention particularly relates to the treatment of ADN with ozone to react with deleterious trace impurities present in the ADN (or to remove such impurities from ADN) which have an adverse effect on the hydrogenation of ADN to form 6-aminocapronitrile (ACN) and hexamethylenediamine (HMD), which are subsequently used in the manufacture of nylon polymers.

BACKGROUND

It is known in the art that nylon, such as nylon 66, can be produced in a multi-step process. In the first step, butadiene (BD) is hydrocyanated with hydrogen cyanide (HCN) in the presence of a homogeneous nickel catalyst to produce adiponitrile (ADN). Subsequently, organic impurities are removed from the ADN to make a refined ADN. Suitable methods for removing the organic impurities include extraction and distillation. See Ostermaier, U.S. Pat. No. 6,331,651, incorporated herein by reference. In the next step, the refined ADN is catalytically hydrogenated to produce HMD or mixtures comprising ACN and HMD. Suitable hydrogenation catalysts include iron-based and Raney type heterogeneous catalysts, such as Raney nickel. In subsequent steps, ACN and HMD are used in the manufacture nylon polymers, such as nylon 6 and nylon 66.

The ADN made in this process contains several impurities that may have an adverse effect on the hydrogenation of the ADN to ACN and HMD. The impurities include: phosphorous (III) compounds (the "P(III) compounds"); 2-cyanocyclopentylideneimine (CPI); and tert-butyl catechol (TBC).

The P(III) compounds are adsorbed on the surface of heterogeneous catalysts and cause poisoning and subsequent deactivation of the iron-based catalyst.

The CPI is hydrogenated to aminomethylcyclopentylamine (AMC) during the hydrogenation of the ADN. The AMC is difficult to separate from the HMD and causes degradation of polymer quality when the HMD is converted to nylon 66 polymer.

The removal of some of these impurities has been addressed in the past. For example, U.S. Pat. No. 6,331,651 ("'651 Patent") describes the ADN which contains P(III) compounds, which is treated with air containing greater than 0.1% wt. ozone in a reactor which provides rapid mass transfer rates, such as an agitated tank fitted with a gas sparger, a pipeline reactor fitted with a static mixer, a tank fitted with a jet mixer or an absorption column. The '651 patent states that it is believed that the P(III) compounds are converted by the ozone treatment to phosphorous compounds in the +5 oxidation state, which are less injurious to the iron-containing hydrogenation catalyst.

Canadian patent 672,712 describes a process for purifying ADN containing impurities, which can be made by several different processes. One of the identified impurities is CPI. The process comprises contacting the ADN with gaseous ozone at a temperature of between 0 and 110° C., preferably 20-50° C.

U.S. Pat. No. 6,359,178 discloses a process for producing hexamethylene diamine (HMD) by hydrogenating adiponitrile, wherein the ADN recycle stream is purified in a conventional manner, such as treatment with an inorganic acid, an organic acid, an acidic ion exchanger or by treatment with an oxidizing agent such as air, ozone or hydrogen peroxide.

USSR Patent Publication 276033 discusses purification of ADN by contacting it in a vessel with an ozonized air, optionally in the presence of an acid, such as phosphoric acid.

Fisher et al., WO 00/03972, disclose the production of HMD, wherein the recycle of ADN is cleaned in a known manner, e.g., by treatment with an inorganic or organic acid, or an oxidizing agent, such as air, ozone, hydrogen peroxide or an inorganic or organic peroxide.

Heckle, U.S. Pat. No. 4,952,541; Yamada et al U.S. Pat. No. 3,725,459; Pounder et al. U.S. Pat. No. 3,758,545; Nishimura et al., U.S. Pat. No. 3,803,206, disclose different processes for purification of adiponitrile and acrylonitrile or reactants used in such processes.

Nonetheless a need still exists for an improved process using ozone to reduce or eliminate problems associated with impurities in ADN.

SUMMARY OF THE INVENTION

The invention is directed to a process and apparatus for reacting undesirable trace impurities present in ADN with ozone, in such a way that ozone is most effectively utilized, using an effective but inexpensive reactor. This is achieved by feeding ADN (which is usually a refined ADN, which is a liquid), which hereafter may be referred to as ADN feed, and an ozone-containing gas continuously to a co-current plug flow static mixer reactor of this invention, which hereafter may be referred to as a PFSMR, which provides extremely rapid and highly selective reaction of the ozone with the P(III), CPI, and TBC present in the ADN. It has been discovered that the TBC is also adsorbed on the surface of heterogeneous catalysts, which causes catalyst deactivation. It has also been discovered that the TBC increases the yield of the ADN hydrogenation reaction to an undesirable co-product, hexamethyleneimine (HMI), when the iron catalyst is employed in that reaction. As a result, the yield of the desired HMD is significantly decreased. In addition to the above mentioned impurities, namely P(III), CPI, and TBC, there is a considerable amount of decenedinitrile isomers (which are $C_{10}$ dinitriles comprising a carbon-carbon double bond), herein referred to as DDN, present in the refined ADN. DDN hydrogenates to impurities that are readily separable from HMD, and it has no adverse affect on hydrogenation catalyst life.

In particular, in one embodiment, the invention is directed to a process for reacting at least a portion of the impurities present in refined ADN to less deleterious compounds comprising: introducing the refined ADN feed and an ozone-containing gas to a PFSMR and contacting the ADN feed with the ozone-containing gas in the PFSMR to oxidize at least a portion of the impurities to produce a reactor discharge which includes a gas and an ozone-treated ADN liquid, which includes the unreacted impurities and less deleterious impurities. The "less deleterious compounds" may also be referred to herein as "less deleterious impurities". The reactor discharge is fed to a suitable apparatus, such as a tank to separate the gas from the liquid. The gas, also referred to as off-gas, may be discharged to the atmosphere, or to a catalytic abatement unit to further reduce the ozone content prior to discharge of the exit gas to the atmosphere, if desired. The de-gassed liquid containing ozone-treated ADN, unreacted impurities, and less deleterious impurities is an ozone-treated ADN product, which is then hydrogenated to ACN and HMD. "Less deleterious compounds" are compounds which have a lesser negative effect on yield and catalyst life in the subsequent ADN hydrogenation process step, than the impurities originally present in the ADN feed. An example of such a less deleterious compound is P(V) formed from the P(III) impurity.

BRIEF DESCRIPTION OF THE DRAWINGS

The embodiments of the present invention are illustrated by way of example, and not by way of limitation, in the figures of the accompanying drawings and in which like reference numerals refer to similar elements and in which:

FIG. 1 shows the consumption of ozone for a plug flow reactor (PFR) versus the fractional conversion of TBC (X TBC) based on a computer simulation of a process for reacting impurities in ADN comprising contacting an ADN feed with an ozone-containing gas, based on conventional reactor selectivity models, as described in Example 2;

FIG. 2 shows the consumption of ozone for a back mixed reactor (CSTR) versus the fractional conversion of TBC (X TBC), for the computer-simulated process described in Example 2;

FIG. 3 shows the improved ozone utilization in a PFR versus in a CSTR for the computer-simulated process described in Example 2.

DETAILED DESCRIPTION OF THE INVENTION

The PFSMR includes static mixers. As is known to those skilled in the art static mixers, often referred to as motionless mixers, are in-line mixing devices which consist of mixing elements (also known as "static mixer elements") inserted in a length of pipe. There are a variety of element designs available from the various manufactures but all are stationary in use. The energy for mixing is derived from the pressure loss incurred as the process fluids flow through the mixing elements and additional pumping energy is necessary over and above that normally needed for pumping requirements. The number of elements required in any application is dependent on several factors, such as the difficulty of the mixing duty. Generally, more elements are necessary for difficult tasks. See, Hamby et al., Mixing in the Process Industries, 2nd edition, Butterworth Heinemann (1992), incorporated herein by reference in its entirety.

The ozone-containing gas comprises ozone and any carrier gas suitable for use in our invention. Suitable carrier gases are any gases that are substantially inert to the refined ADN at the operating temperatures of this invention, such as air, air diluted with nitrogen, oxygen-enriched air, nitrogen, carbon dioxide, helium, argon, or a combination of two or more of such gases. In one embodiment, the carrier gas is air. The ozone-containing gas may include about 0.1 to about 3.0% wt. of ozone, such as about 1.0 to about 3.0% wt., or about 3.0% wt. of ozone.

In an embodiment, the ADN feed may include at least one of the following impurities: 2-cyanocyclopentylideneimine (CPI), phosphorous (III) compounds (P(III)), decenedinitrile (DDN) or tert-butyl catechol (TBC). Amounts of impurities in the ADN feed and in the ozone-treated ADN product may be measured by any suitable method. For example, phosphorous may be determined by inductively coupled plasma mass spectrometry (ICP) and it is believed that all of the phosphorous present is P(III). CPI and TBC may be determined by liquid chromatography. DDN may be determined by gas chromatography.

The ADN feed may comprise at least one of: about 0.5 to about 10, such as about 2 to about 10 parts per million by weight (ppm) P(III), about 10 to about 200, such as about 10 to about 50 ppm CPI, about 5 to about 100, such as about 10 to about 50 ppm TBC, about 100 to about 600 ppm, such as about 200 to about 400 ppm DDN or a combination thereof. In one embodiment the ADN feed comprises less than 0.1% wt. of all such impurities: (i.e., P (III), CPI, TBC and DDN).

In one embodiment, the ozone-treated ADN comprises less than 1 ppm P(III), less than 5 ppm CPI, and less than 5 ppm TBC.

In another embodiment, the amount of ozone supplied to the process is sufficient to react at least about 10 to about 80% of the impurities present in the ADN feed.

In another embodiment, the amount of ozone supplied to the process is sufficient to react at least about 90% of the TBC from the ADN feed. In yet another embodiment about 0.1 to about 4, such as about 0.1 to about 2 mmoles of ozone per liter of ADN feed is supplied to the PFSMR.

The ADN feed can be produced by any suitable method, such as by the hydrocyanation of butadiene in the presence of a homogeneous nickel(0) catalyst with phosphorous containing ligands. The ADN used in the process of this invention is usually ADN refined by distillation, as described above. The ozone used in the process can be produced by any known methods. In one embodiment, the ozone is produced by passing air through an ozone generator that produces a gaseous stream comprising about 3 wt % ozone.

The process conducted in the PFSMR very efficiently utilizes the ozone. For example, the ozone consumption in the reactor is in excess of 99% of the ozone fed to the reactor. Thus, the content of unreacted ozone in the off-gas is very low. This is significant and advantageous for environmental reasons. There are strict environmental limitations on the discharge of ozone to the atmosphere. The lower the content of ozone in the reactor off-gas, the less costly the treatment of the off-gas to destroy ozone before discharge to the environment.

Without being bound by any theory, it is believed that ozone reacts very rapidly with all of the impurities present in ADN that are listed above. The reactions are so fast that, it is believed, they take place substantially completely in the liquid phase at the gas-liquid interface, and can be described as chemically assisted mass transfer controlled reactions. While all of the reactions are fast, some are faster than others. At a given impurity concentration, the rates of reaction of ozone with the above impurities decrease in the following order: P(III) and CPI>TBC>DDN, where the reaction with DDN is the slowest. This means that when all of these components (i.e., impurities) are present simultaneously, the ozone reacts selectively with these impurities, reacting faster with the faster reacting species.

While ozone reacts slowest with the DDN, the concentration of DDN in the feed ADN is usually more than 4 times the concentration of the combined P(III), CPI, and TBC on a molar basis. This means that the amount of ozone reacting with the DDN increases as the other impurities are depleted. If it is desired to react the other impurities completely with ozone, a considerable amount of ozone may react needlessly with the DDN. Any ozone consumed by the DDN is wasteful since the DDN hydrogenates to impurities that are readily separable from HMD, and the DDN has substantially no adverse effect on hydrogenation catalyst life.

When several different reactions take place in parallel with a single reactant, selectivity toward the more reactive species is favored by running the reaction in a plug flow configuration. A back-mixed configuration, as would be achieved in a continuous agitated tank (CSTR), or a countercurrent configuration, as would be achieved in an absorption tower, cause poorer utilization of the ozone reactant, i.e., higher ozone consumption to achieve the same level of conversion of the undesirable impurities. Therefore, a co-current plug flow configuration is favored for this application.

The reactions occurring in the PFSMR are very fast, and, it is believed (without being bound by any operability theory), the reaction rate is controlled by the rate of mass transfer of ozone from the gas phase to the liquid phase. High mass transfer is favored by high levels of turbulence, and large interfacial areas. Thus, a reactor configuration is required that meets these requirements.

A reactor type used in the process of the invention that provides both co-current flow and exceptionally high mass transfer rates is a plug flow reactor containing static mixers (also referred to herein as "mixers"). These mixers are sections of pipe that contain internal static mixer elements that promote high mass transfer rates. Each section of the pipe may include the static mixer elements, or some sections of the pipe may not include such static mixer elements. Furthermore, static mixer elements included in different pipe sections may be the same or different. Other advantages of these static mixer reactors are they are inexpensive, easy to operate, and require little maintenance. By using such a reactor, ozone utilization for the desired reactions is maximized, and reactor cost is low. Example 2 illustrates the lower ozone consumption obtained with a plug flow reactor versus a backmixed tank reactor. For typical impurity levels, ozone consumption is reduced by about 30% compared to a backmixed reactor.

In addition to providing high reaction rates and ozone selectivity, the PFSMR gives very high conversions of ozone compared to backmixed reactors. Ozone conversions in the PFSMR can exceed 99.9% of the ozone in the feed gas. The amount of ozone present in the gas phase exit of the reactor can be reduced to less than 10 ppm using a properly designed PFSMR, which is about 100 times lower than can be achieved using a backmixed reactor. This reduces the size of the environmental abatement equipment needed to destroy the residual ozone in the reactor exit gas.

In one embodiment, the process of this invention comprises feeding liquid ADN and gaseous air containing about 3% by weight ozone continuously to the PFSMR. The reactor is operated at ambient conditions. The amount of ozone is adjusted to react almost completely with the P(III), CPI, and TBC, while minimizing the unavoidable reaction of ozone with the DDN. However, the presence of the DDN has the advantage of providing a buffer to consume any excess ozone fed to the process, and eliminate any residual ozone in the exit gas, which alleviates, or eliminates the problem of ozone discharge to the atmosphere.

The design of a plug flow reactor with static mixer elements, such as the PFSMR of this invention, includes a number of steps. Step one is to determine the amount of ozone required to react with the impurities present; this is determined by the levels of impurities present and the reaction stoichiometry. Step two is to determine the reactor volume required to give the desired concentration of ozone in the exit gas, which is achieved using appropriate reactor design equations and mass transfer correlations. Chapters 23 and 24 of the book "Chemical Reaction Engineering, $3^{rd}$ Edition" by Octave Levenspiel (incorporated herein by reference) discusses the reactor design equations. The mass transfer parameter, $k_L a$, for static mixers which can be used in this invention may be obtained using proprietary correlations supplied by static mixer vendors, and it typically ranges from 0.1 to 2 seconds$^{-1}$ (Harnby et al.). In step three, the reactor diameter is chosen to give suitably high mass transfer rates, coupled with acceptable pressure drop across the reactor. Desirable pressure drop across the reactor is at least about 1 atmosphere (101.3 kPa). Suitable mass transfer rates in the reactor are obtained with a mass transfer parameter $k_L a$ of about 0.1 seconds$^{-1}$ or greater, preferably about 0.5 seconds$^{-1}$ or greater, such as about 0.1 to about 2 seconds$^{-1}$. This is done using vendor correlations for the equipment chosen. Once the reactor volume and diameter are known, reactor length is determined. Once the reactor length and diameter are determined, the reactor is purchased from a vendor as lengths of pipe containing internal static mixer elements. Another important parameter is residence time (also known as "holdup" time). Residence time for the PFSMR used in our process is about 2 to about 8 seconds, such as about 2 to about 4 seconds e.g., 2.5 or 3 seconds. A desired ozone dosage can be calculated based on impurity levels in the refined ADN. The feed rate of ozone is adjusted to achieve the desired ozone dosage for a given feed rate of and impurity content in refined ADN liquid. One way to adjust the ozone feed rate is to adjust the concentration of ozone in the ozone-containing gas fed to the PFSMR. The process of this invention is particularly easy to control because increasing liquid feed rate simultaneously causes a reduction in holdup time and an increase in $k_L a$ such that the conversion of ozone remains relatively constant. Decreasing the liquid feed rate simultaneously causes an increase in holdup time and a decrease in $k_L a$ such that the conversion of ozone remains relatively constant. The refined ADN and ozone-containing gas feeds to the reactor operate at sufficient pressure to overcome the design pressure drop across the reactor, as determined in step three. Typically this reactor operates at a temperature less than 50° C., such as ambient temperature. The ozone containing gas and ADN are fed simultaneously or substantially simultaneously into the reactor inlet, and the reactor discharge is fed to a tank, or any other suitable apparatus, to separate the gas from the liquid. The gas, which includes the carrier gas and unreacted ozone, is discharged to the atmosphere, or to a catalytic abatement unit to further reduce the ozone content prior to discharge of the exit gas to the atmosphere, if desired. The resulting liquid, including ozone-treated ADN, unreacted impurities and the less deleterious impurities, is then reacted with hydrogen to form ACN and HMD.

EXAMPLE 1

Air was passed at a rate of 30 standard cubic meters per hour through a model SMA 500 S Wedeco ozone generator, to produce an ozone concentration of 1.0 wt % in the air. The ozone containing air stream was fed to the PFSMR, together with a refined adiponitrile stream. The adiponitrile feed rate was 13.2 metric tons per hour. The static mixer contained Sulzer SMV elements. There were a total of six mixer sections, and each section was 6 feet (1.8 m) in length, giving a total static mixer length of 36 feet (11 m). Each 6-foot (1.8-m) long section contained six static mixer elements, each of which was 6 inches (15.2 cm) in length, where each of the elements was separated from each other by 6 inches (15.2 cm) of open pipe, i.e., the pipe without static mixer elements. The diameter of the static mixer was 3 inches (7.6 cm). Based on the measured performance the mass transfer parameter $k_L a$ was calculated to be about 0.7 seconds$^{-1}$. The adiponitrile feed contained 5.7 ppm phosphorous as organic phosphorous-containing compounds, 31 ppm CPI, 2 ppm TBC, and 186 ppm DDN, where ppm designates part per million by weight. After the ozone treatment, the ozone-treated adiponitrile contained <1 ppm CPI, 2 ppm TBC, and 130 ppm DDN. The concentration of TBC was not noticeably reduced because the TBC concentration in the feed was very low, and so its reaction rate was low in comparison to the DDN, which was present in the feed at much higher (almost 100×) concentrations in the feed. It is believed that essentially all of the CPI was destroyed by the ozone, then all of the phosphorous was oxidized from the +3 to +5 oxidation state, since laboratory results show that ozone reacts with CPI and phosphorous at about the same rate. The total hold up time of material in the reactor was 3.7 seconds, and the ozone concentration in the gas exiting the reactor, i.e., air, was 2.5 ppm, which corresponds to a 99.98% conversion of the ozone.

The ozone-treated ADN was hydrogenated with an iron oxide based catalyst. Ozone treatment was started when the ADN hydrogenation catalyst was about half deactivated based on extensive previous plant data. After ozone treatment was initiated, the rate of catalyst deactivation declined to less than half the normal rate, which extended the catalyst life more than two-fold.

EXAMPLE 2

This example illustrates the improved ozone utility that is realized by carrying out the reaction in a plug flow reactor (PFR) versus a backmixed reactor (CSTR). This example is a computer simulation of a process based on conventional reactor selectivity models using experimentally determined relative reaction rate data for various impurities with ozone. In this example, the ADN feed, fed to both simulated reactors, contains the following impurities: 10 ppm P(III), 50 ppm CPI, 25 ppm TBC, and 675 ppm DDN.

The reaction stoichiometries for the reaction of ozone with the impurities present are one mole of ozone each per mole for P(III), CPI, and DDN; for TBC the stoichiometry is three moles of ozone per mole of TBC. Experiments were conducted in which refined ADN was reacted with ozone in a CSTR at atmospheric pressure and ambient temperature. The depletion of P(III), CPI, TBC, and DDN in the CSTR was measured. These data were fitted to a CSTR reactor design model, derived according to Levenspiel, to determine relative reaction rate constants for the reactions of ozone with P(III), CPI, TBC, and DDN. The P(III) and CPI react virtually completely before attack of ozone on the TBC and DDN begins. Then the TBC and DDN compete for the available ozone. The reaction rate constant for the reaction of ozone with TBC is about 85 times larger than the reaction rate constant for the reaction of ozone with DDN, however there is considerably more DDN available to compete for the available ozone. Using the above data it is possible to calculate the amount of ozone consumed per liter of ADN feed for the two simulated reactor configurations at various fractional conversions of DDN. FIG. 1 shows the ozone consumption for a plug flow reactor (PFR), and FIG. 2 shows the consumption for a backmixed reactor (CSTR) versus the fractional conversion of TBC (X TBC). These data show that the ozone consumption required for 90% reaction of the TBC is 1.46 mmoles of ozone per liter of ADN for the PFR, versus 2.11 mmoles of ozone per liter of ADN for the CSTR. This corresponds to 0.65 mmole/liter reduction in ozone demand for 90% reaction of TBC. FIG. 3 clearly illustrates the improved ozone utilization in a PFR vs. a CSTR.

EXAMPLE 3

This example shows the beneficial effect of reducing HMI yield during the manufacture of HMD achieved by treating the ADN with ozone to destroy TBC prior to hydrogenation.

One part by weight ADN was continuously mixed with six parts by weight anhydrous ammonia. This mixture was fed to a bed of heterogeneous iron catalyst, together with a stoichiometric excess of hydrogen gas. A stoichiometric amount of hydrogen is four moles of hydrogen per mole of ADN. The reactor operated at a pressure of approximately 5000 psi (34.5 MPa). The reactor feed temperature was approximately 100° C., and the temperature increased along the length of the bed due to the heat of reaction of ADN and hydrogen.

Initially ozone treated ADN was fed to the reactor for a period of 250 hours. During the period when ozone treated ADN was fed to the reactor the yield from ADN to HMI averaged 0.10% (moles HMI formed per mole ADN reacted× 100%). The ADN feed was then switched to ADN that was not ozone treated, and run for an additional 150 hours, and over this period of operation the average yield from ADN to HMI increased to 0.5%. The amount of TBC in the ozone treated ADN was less than 1 ppm, and the amount of TBC in the untreated ADN was about 25 ppm.

While the illustrative compositions, processes, reactors, methods and procedures, have been described with particularity, it will be understood that various other modifications will be apparent to and can be readily made by those ordinarily skilled in the art without departing from the spirit and scope of our disclosure. Accordingly, we do not intend for the scope of the claims of this application to be limited to the examples and descriptions set forth in the application, but rather that the claims be construed as encompassing all novel and unobvious features of the embodiments covered by the claims, including equivalents of such embodiments.

The invention claimed is:

1. A process for reacting impurities present in adiponitrile (ADN) comprising: introducing ADN feed and an ozone-containing gas to a co-current plug flow static mixer reactor (PFSMR) and contacting the ADN feed with said ozone-containing gas in said PFSMR to oxidize at least a portion of said impurities, to produce a reactor discharge, wherein said impurities include 2-cyanocylcopentylideneimine (CPI), phosphorous (III) compounds (P(III)), from about 5 to about 100 ppm of tert-butyl catechol (TBC) and from about 100 to about 600 ppm of decenedinitrile (DDN).

2. A process of claim 1, wherein the reactor discharge includes a gas and an ozone-treated ADN liquid, which includes unreacted impurities and less deleterious impurities.

3. A process of claim 2, wherein the reactor discharge is conducted to an apparatus which separates the gas from the ozone-treated ADN liquid to produce an off-gas and a degassed liquid, which is an ozone-treated ADN product.

4. A process of claim 3, wherein the off-gas contains less than 10 ppm of ozone and is discharged to the atmosphere or to a catalytic abatement unit.

5. A process of claim 1, wherein the ozone-containing gas comprises ozone and a carrier gas, and wherein said carrier gas is any gas that is substantially inert to the ADN feed at operating temperature of the process.

6. A process of claim 5, wherein the carrier gas is air, air diluted with nitrogen, oxygen-enriched air, nitrogen, carbon dioxide, helium, argon, or a mixture thereof.

7. A process of claim 5, wherein the ozone-containing gas comprises about 0.1 to about 3% wt. of ozone.

8. A process of claim 5, wherein the ozone-containing gas comprises about 3.0% wt. of ozone.

9. A process of claim 1, wherein the ADN feed comprises about 0.5 to about 10 ppm P(III) and about 10 to about 200 ppm CPI.

10. A process of claim 1, wherein the ADN feed comprises about 2 to about 10 ppm P(III), about 10 to about 50 ppm CPI, about 10 to about 50 ppm TBC, and about 200 to about 400 ppm of DDN.

11. A process of claim 3, wherein the ozone-treated ADN product comprises less than 1 ppm P(III), less than 5 ppm CPI, and less than 5 ppm TBC.

12. A process of claim 1, wherein the amount of ozone supplied to the process is sufficient to react at least about 90% of the TBC present in the ADN feed.

13. A process of claim 1, wherein about 0.1 to about 4 mmoles of ozone per liter of the ADN feed is supplied to the process.

14. A process of claim 1 wherein the ADN feed is produced by the hydrocyanation of butadiene using a homogeneous nickel(0) catalyst with phosphorous containing ligands.

15. A process of claim 1 where the ozone is produced by passing air through an ozone generator that produces a gaseous stream comprising about 3 wt % ozone.

16. A process of claim 1, wherein the ozone consumption in the PFSMR is in excess of 99% of the ozone fed to the PFSMR.

17. A process of claim 1, wherein the mass transfer parameter ($k_L a$) is about 0.1 second$^{-1}$ or greater.

18. A process of claim 1, wherein the mass transfer parameter ($k_L a$) is about 0.5 second$^{-1}$ or greater.

19. A process of claim 1, wherein the residence time of the ADN feed and the ozone-containing gas in the PFSMR is about 2 to about 8 seconds.

20. A process of claim 1, wherein the residence time of the ADN feed and the ozone-containing gas in the PFSMR is about 2 to about 4 seconds.

21. A process of claim 1, wherein the residence time of the ADN feed and the ozone-containing gas in the PFSMR is about 3 seconds.

22. A process of claim 3, wherein the ozone-treated ADN product is hydrogenated to ACN and HMD.

23. A process of claim 1, wherein the pressure drop across the PFSMR is at least about 1 atmosphere (101.3 kPa).

* * * * *